| United States Patent [19] | [11] 4,152,361 |
|---|---|
| Imai | [45] May 1, 1979 |

[54] PRODUCTION OF CYCLOHEXENE

[75] Inventor: Tamotsu Imai, Mt. Prospect, Ill.

[73] Assignee: UOP Inc., Des Plaines, Ill.

[21] Appl. No.: 889,761

[22] Filed: Mar. 24, 1978

[51] Int. Cl.$^2$ .............................................. C07C 13/20
[52] U.S. Cl. ............................. 585/353; 208/DIG. 2; 585/476
[58] Field of Search ........... 260/666 A, 668 C, 668 R, 260/668 D; 208/DIG. 2

[56] References Cited

U.S. PATENT DOCUMENTS

| 2,839,590 | 6/1958 | Fetterly | 260/668 D |
| 3,702,886 | 11/1972 | Argauer et al. | 423/328 |
| 3,804,747 | 4/1974 | Kimberlin et al. | 208/120 |

Primary Examiner—Veronica O'Keefe
Attorney, Agent, or Firm—James R. Hoatson, Jr.; Raymond H. Nelson; William H. Page, II

[57] ABSTRACT

Cyclohexene may be produced from phenylcyclohexane by treating the latter compound at an elevated temperature in the presence of certain solid acidic catalysts such as zeolite or silica-alumina to produce the desired compound.

4 Claims, No Drawings

PRODUCTION OF CYCLOHEXENE

This invention relates to a process for obtaining cyclohexene. More specifically, the invention is concerned with a process for obtaining cyclohexene from cyclohexyl substituted benzenes utilizing a solid acidic catalyst of the type hereinafter set forth in greater detail.

Cyclohexene is an important intermediate in the preparation of various chemicals. In addition to being used in organic synthesis, the compund may also be used as a catalyst solvent or in oil extraction. It has now been discovered that the desired product may be obtained by treating a cyclohexyl substituted aromatic compound with certain solid acidic catalysts at an elevated temperature to obtain the desired product.

It is therefore an object of this invention to provide a process for producing cyclohexene.

A further object of this invention is found in a process for producing cyclohexene utilizing certain solid acidic catalysts.

In one aspect an embodiment of this invention resides in a process for the production of cyclohexene which comprises treating phenylcyclohexane at an elevated temperature in the presence of a solid acidic catalyst, and recovering the resulting cyclohexene.

A specific embodiment of this invention is found in a process for the production of cyclohexene which comprises treating phenylcyclohexane at a temperature in the range of from about 300° to about 600° C. in the presence of a solid acidic catalyst comprising a sodium Y-zeolite, and recovering the resulting cyclohexene.

Other objects and embodiments will be found in the following detailed description of the present invention.

As hereinbefore set forth the present invention is concerned with a process for the production of cyclohexene. The desired product is obtained by decomposing phenylcyclohexane in the presence of certain solid acidic catalysts of the type hereinafter set forth in greater detail, the decomposition of the phenylcyclohexane resulting in the obtention of cyclohexene and benzene. The starter material, namely, phenylcyclohexane may itself be obtained by the selective hydrogenation of biphenyl.

In the preferred embodiment of the invention the decomposition of phenylcyclohexane is effected by treating this compound with a solid acidic catalyst at an elevated temperature in the range of from about 300° to about 600° C. and from about 1 to about 50 atmospheres. The catalyst which is employed to effect the decomposition comprises a solid acidic catalyst possessing a control acidic strength and relatively large pore openings. The acid strength of the catalyst must be controlled inasmuch as if the catalyst possesses a high acid strength, the decomposition of the phenyl cyclohexane will be accompanied by the formation of undesired side reaction products such as methylcyclopentene, methylcyclopentane, cyclohexane, etc., thereby decreasing the yield of the desired product and rendering the process economically unfeasible to operate. In addition to the control acidic strength, the catalyst should also possess relatively large pore openings, that is, openings which are larger than about 8 to about 9 Angstroms in diameter, thus enabling the molecule to enter the catalyst pores. By utilizing such a catalyst, it is possible to obtain the selective decomposition of phenylcyclohexane to form benzene and the desired cyclohexene.

A particularly effective type of catalyst which may be utilized to effect the process of the present invention comprises a crystalline aluminosilicate. Crystalline aluminosilicates are well known in the art and descriptions thereof have been published in considerable detail. In general, they comprise silica, alumina and one or more exchangeable cations such as sodium. They are characterized by a three-dimensional network of fundamental structural units consisting of silicon-centered $SiO_4$ and aluminum-centered $AlO_4$ tetrahedra interconnected by the apical oxygen atoms. To effect a chemical balance, each $AlO_4$ tetrahedra has associated therewith the aforementioned exchangeable cation. In most cases, at least a portion of the exchangeable cations are subsequently ion-exchanged with hydrogen cations to yield the hydrogen or active form of the crystalline aluminosilicate. The $SiO_4$ and $AlO_4$ tetrahedra are arranged in a definite geometric pattern often visualized in terms of chains, layers or polyhedra, all formed by the linking of the tetrahedra fundamental structural units. In any case, the effect is a network of cages or cavities interconnected by intracrystalline pores and channels whose narrowest cross-section has essentially a uniform diameter. The various crystalline aluminosilicates may be classed by the geometric pattern of their framework with its attendant pore size, and by the silica/alumina mol ratio of which they are composed.

The crystalline aluminosilicates herein contemplated are the syntheticaly prepared faujasites generally referred to as "Type X" and "Type Y" crystalline aluminosilicates. Of particular interest is the synthetically prepared "Type Y" crystalline aluminosilicate characterized by a silica/alumina mol ratio in excess of about 3, generally from about 3 to about 7, as opposed to a silica/alumina mol ratio of less than about 3, generally from about 2 to about 3, characteristic of "Type X" crystalline aluminosilicate—the geometric framework or structure of "Type X" and "Type Y" being essentially identical.

Methods of synthesizing said crystalline aluminosilicates are generally well known. Briefly, a reaction mixture is prepared comprising sodium hydroxide in aqueous solution, sodium aluminate or other suitable alumina precursor, and sodium silicate or other suitable silica precursor including colloidal silica. The reaction conditions, as well as the mol ratio of the reactants, are carefully controlled to precipitate a particular crystalline aluminosilicate product. Typically, the reaction mixture is allowed to digest at ambient temperature up to about 40 hours or more after which it is heated with stirring at a temperature of from about 180° to about 250° F. The mother liquor, comprising residual alkali metal silicate, is then filtered or decanted from the crystalline aluminosilicate solids product which is thereafter washed and dried and recovered as finely divided particles of about 0.05–0.5 microns in size.

The crystalline aluminosilicate which is characterized by a crystalline form described as a truncated octahedra with pore openings in the range of from about 6 to about 15 Angstroms and which has been prepared according to the process described in the above paragraph may, if so desired, then be subsequently treated in contact with an ion exchange solution containing ions which are capable of replacing some of the alkali metal cations such as sodium, potassium, lithium, etc., ions. In the preferred embodiment of the invention, the zeolites will comprise sodium Y zeolites. sodium X zeolites, potassium Y zeolites, potassium X zeolites, lithium Y zeolites, and lithium X zeolites. However, it is also contemplated within the scope of this invention that the alkali metal ions may be partially exchanged with other metal cations selected from Groups, IB, IIB, IIIA, IIIB, IVB, VB, VIB, VIIB, and VIII of the Periodic Table, the only criterion being that a major portion of the metal cations present in the zeolite will comprise an alkali metal. By utilizing zeolites containing a relatively large amount of alkali metal cations either alone or in conjunction with a small amount of the other metal cations from the groups hereinbefore enumerted, it is possible to control the acid strength of the catalyst.

In addition it is also contemplated within the scope of this invention that other types of crystalline zeolites may also be employed as catalysts for the selective decomposition of phenylcyclohexane. Some specific examples of these zeolites are those which are sold under the tradenames of ZSM-5, ZSM-11 and ZSM-12 by the Mobil Oil Company, the preparation of these zeolites being set forth in U.S. Pat. Nos. 3,702,886, 3,709,979 and 3,832,449 respectively.

In this respect, it is to be noted that other zeolites such as mordenite or A type zeolites are ineffective as catalysts for the selective decomposition of phenylcyclohexane to form cyclohexene. Acidic catalysts of the mordenite or A type zeolitic forms will be ineffective due to the fact that the aperture size of these solids is too small or the diffusional resistance is too high for the molecule to enter the interstitial cavities. For example, the pore structure of mordenite is tubular in form and the diffusion resistance is too high for the molecule to enter the cavity.

While the preferred form of solid acidic catalyst of the present invention comprises an alkali metal zeolite of the Y or X type, it is also contemplated within the scope of this invention that silica-alumina which has been poisoned with an alkali metal cation will also be effective as a catalyst for the selective decomposition process of the present invention. However, it has been discovered that this silica-alumina which is amorphous in nature must contain some of the alkali metal cation inasmuch as nonpoisoned silica-alumina is ineffective due to its strong acidic nature.

A process of this invention may be effected in any suitable manner and may comprise either a batch or continuous type operation. For example, when a batch type operation is used a quantity of the catalyst is placed in an appropriate apparatus and the phenylcyclohexane which, if so desired, may be admixed with an inert gas such as nitrogen is charged to the reactor. In addition, stream and/or volatile alkaline compounds such as ammonia, amines such as methylamine, ethylamine, etc., pyridine, etc. are introduced along with the feed as a method for controlling the acid strength of the catalyst, said water or alkaline compounds being added to the feed stream in an amount in the range of from about 10 to about 10,000 ppm based upon the phenylcyclohexane. The reactor is then heated to the desired operating temperature which may be in the range of from about 300° to about 600° C. and at a pressure in the range of from about 1 to about 50 atmospheres, and maintained thereat for a predetermined period of time which may range from about 0.5 up to about 10 hours or more in duration. Upon completion of the reaction time the mixture is recovered and subjected to conventional means of separation such as fractional distillation whereby the desired cyclohexene is separated from other products such as benzene and unwanted side products such as the isomeric methylcyclopentene and recovered.

It is also contemplated within the scope of this invention that the selective decomposition process may be effected in a continual manner of operation. When such a type of operation is employed the catalyst is positioned in a reactor which is maintained at the proper operating conditions of temperature and pressure, the charge comprising phenylcyclohexane is continuously charged to the reactor and after passage through the reactor for a predetermined period of time the reactant effluent is continuously withdrawn and subjected to conventional means of separation whereby the desired cyclohexene is separated from other reaction products and unreacted phenylcyclohexane, the latter being recycled to form a portion of the feed stock. When employing a continuous type of selective decomposition, it is possible to utilize various forms of reaction. For example, the catalyst may be positioned in the reactor in a fixed bed while the charge stock is passed over the catalyst in either an upward or downward flow. A second method of operation which may be employed comprises a moving bed type of operation in which the catalyst bed and the charge stock are passed through the reactor either concurrently or countercurrently to each other. Yet another form of continuous operation which may be employed comprises the slurry type in which the catalyst is carried into the reactor as a slurry in the liquid charge.

The following examples are given for purposes of illustrating the selective decomposition process of the present invention. However, it is to be understood that these examples are given merely for purposes of illustration and that the present invention is not necessarily limited thereto.

EXAMPLE I

To illustrate the operability of the particular solid acidic catalysts which are used in the present invention, 11.40 grams of a sodium Y zeolite catalyst were placed in a glass reactor. The reactor and catalyst were heated to a temperature of 500° C. and a charge stock comprising a mixture of phenylcyclohexane and nitrogen in a molar feed ratio of 2 was passed over the bed of catalyst at a liquid hourly space velocity of 2 for a period of 2 hours. At the end of this period a gas liquid chromatographic analysis disclosed the presence of 6.8 wt. % of cyclohexene and 11.4 wt. % of benzene. When the above experiment was repeated a gas liquid chromatographic analysis of the product showed a 6.8 wt. % of cyclohexene and a 12.2 wt. % of benzene.

EXAMPLE II

In this example a hydrogen Y zeolite was used as the catalyst, 10.78 grams of the catalyst being placed in a glass reactor which was heated to 450° C. A similar charge stock comprising a mixture of phenylcyclohexane and nitrogen was passed over the catalyst bed at a liquid hourly space velocity of 2 for a period of 2 hours. At the end of this time the product was analyzed by means of a gas liquid chromatograph and was found to contain 1.7 wt. % of cyclohexene and 11.7 wt. % of benzene. A repeat of the experiment disclosed the obtention of 1.5 wt. % of cyclohexene and 5.1 wt. % of benzene.

EXAMPLE III

In this example a solid acidic catalyst in which a portion of the sodium cation was replaced with magnesium was utilized for the selective decomposition of phenylcyclohexane. 10.43 grams of the catalyst were placed in a glass reactor which was heated to a temperature of about 400° C. while a similar charge stock was passed over the bed of catalyst at a liquid hourly space velocity of 2 for a period of 2 hours. At the end of this time a gas liquid chromatographic analysis disclosed the presence of cyclohexene and 3.4 wt. % of benzene. A similar experiment using a like catalyst but effecting the decomposition at a temperature of 450° C. under similar conditions disclosed the presence of 7.6 wt. % of cyclohexene and 20.3 wt. % of benzene.

EXAMPLE IV

To illustrate the necessity for utilizing a catalyst which possesses relatively large pore openings and a controlled acidic strength, a further series of experiments concerning the selective decomposition of phenylcyclohexane were performed. The operating parameters of the reaction were identical in nature, that is, a phenylcyclohexane/nitrogen charge stock was passed over a bed of the catalyst at atmospheric pressure and a liquid hourly space velocity of 2 for a period of 2 hours. In the first of these series of experiments, the catalyst consisted of 3.4% of potassium composited on alumina. When the reaction was run at temperatures of 400° C. to about 450° C. no conversion of the phenylcyclohexane was obtained. Very poor conversion of the phenylcyclohexane was observed when effecting the thermal decomposition at temperatures ranging from 400° to about 450° C. over a Celite catalyst.

When the experiment was run at temperatures from 400° to about 450° C. in the presence of a sodium mordenite catalyst, only from 0.1 to 0.6 wt. % cyclohexene was obtained and from 0.1 to 0.9 wt. % of benzene.

It is, therefore, readily apparent from a comparison of the above examples that the selective decomposition of phenylcyclohexane to form cyclohexene and benzene can only be effectively performed when utilizing the catalyst of the type hereinbefore described, that is, a solid acidic catalyst which possesses relatively large pore openings and a controlled acidity.

I claim as my invention:

1. A process for the production of cyclohexene which comprises contacting phenylcyclohexane at a temperature of from about 300° to about 600° C. with a metal cation-containing aluminosilicate having pore openings of from about 6 to about 15 Angstroms, the major portion of the metal cations of said aluminosilicate being alkali metal, and recovering the resultant cyclohexene.

2. The process as set forth in claim 1 in which said aluminosilicate is a faujasite.

3. The process as set forth in claim 1 in which said aluminosilicate is a sodium Y-zeolite.

4. The process as set forth in claim 1 in which said aluminosilicate is a sodium X-zeolite.

* * * * *